US00PP15758P3

(12) United States Plant Patent
Smaal

(10) Patent No.: US PP15,758 P3
(45) Date of Patent: May 10, 2005

(54) ***KALANCHOE* PLANT NAMED 'PATTY'**

(50) Latin Name: *Kalanchoe blossfeldiana*
Varietal Denomination: Patty

(75) Inventor: Andres Smaal, Aalsmeer (NL)

(73) Assignee: A.B. Breeding BV, De Kwakel (NL)

( * ) Notice: Subject to any disclaimer, the term of this patent is extended or adjusted under 35 U.S.C. 154(b) by 0 days.

(21) Appl. No.: 10/644,507

(22) Filed: Aug. 20, 2003

(65) Prior Publication Data

US 2004/0083522 P1 Apr. 29, 2004

Related U.S. Application Data

(63) Continuation of application No. 09/993,406, filed on Nov. 19, 2001, now abandoned.

(51) Int. Cl.[7] ..... A01H 5/00

(52) U.S. Cl. ..... Plt./340
(58) Field of Search ..... Plt./340

(56) References Cited

PUBLICATIONS

UPOV–ROM GTITM Computer Database, 2003/06, GTI Jouve Retrieval Software, citation for 'Patty'.*
Netherlands PBR Publication Document relating to Application KLN 283 (2 pages)—in Dutch.

* cited by examiner

*Primary Examiner*—Bruce R. Campell
*Assistant Examiner*—S B McCormick-Ewoldt
(74) *Attorney, Agent, or Firm*—Wood, Phillips, Katz, Clark & Mortimer

(57) ABSTRACT

A new and distinct cultivar of *Kalanchoe* plant named 'Patty' is provided. This new cultivar is characterized by its bright orange flowers, dark green foliage, compact growth habit and excellent basal branching.

1 Drawing Sheet

Latin name of genus and species of plant claimed: *Kalanchoe blossfeldiana.*
Variety denomination: 'Patty'.

BACKGROUND OF THE INVENTION

The present invention comprises a new and distinct *Kalanchoe* plant, botanically known as *Kalanchoe blossfeldiana,* and hereinafter referred to by the cultivar name 'Patty'.

The new cultivar was developed by the inventor through a controlled breeding program during August 1995 in The Netherlands. The female (seed) parent of 'Patty' was the proprietary *Kalanchoe blossfeldiana* selection designated '95013' (not patented), characterized by its small orange flowers and good branching habit. The male (pollen) parent of 'Patty' was the proprietary *Kalanchoe blossfeldiana* selection designated '95316-16' (not patented), characterized by its red flowers and dark green foliage. 'Patty' was discovered and selected as a flowering plant within the progeny of the stated cross by the inventor in June 1996.

Asexual reproduction of the new cultivar at Arroyo Grande, Calif. and West Chicago, Ill., has been through the use of terminal vegetative cuttings and has demonstrated that the characteristics of the new cultivar as herein described are firmly fixed and retained through successive generations of such asexual propagation.

SUMMARY OF THE INVENTION

It was found that the cultivar of the present invention:

(a) exhibits bright orange flowers, (b) forms dark green foliage, (c) exhibits a good basal branching character, and (d) exhibits a compact upright growth habit.

The new cultivar of the present invention can be compared to 'Arjuno' (U.S. Plant Pat. No. 6,632). In side by side comparisons with 'Arjuno', it is found that the new cultivar is more compact, in terms of plant height, less floriferous in terms of the approximate number of flowers per plant, and exhibits flowers of a different color. Specifically, the petal color of the fully opened upper surface of the new cultivar is RHS 39A whereas the petal color of the fully opened upper surface of 'Arjuno' is between 44A and 44B. A detailed comparison is found in Table 1.

BRIEF DESCRIPTION OF PHOTOGRAPH

The accompanying photograph shows as nearly true as it is reasonably possible to make the same in color illustrations of this type, typical flower and foliage characteristics of the new cultivar. The plants were grown in a greenhouse at West Chicago, Ill., U.S.A.

DETAILED BOTANICAL DESCRIPTION

The cultivar 'Patty' has not been observed under all possible environmental conditions to date. Accordingly, it is possible that the phenotype may vary somewhat with variations in the environment, such as temperature, light intensity, and day length.

The chart used in the identification of colors described herein is The R.H.S. Colour Chart of The Royal Horticultural Society, London, England. The color values were determined on Jan. 4, 2001 between 9:00 and 9:30 am under natural daylight. The plants used for the following observations and measurements were produced from cuttings taken from stock plants and grown in West Chicago, Ill. in 10 cm pots for nineteen (19) weeks. Plants were grown in a double poly carbonate covered greenhouse under conditions comparable to those used in commercial practice while utilizing a soilless growth medium and maintaining temperatures of approximately 82° F. during the day and approximately 66° F. during the night. Plants were exposed to three weeks of long days followed by 9 weeks of short days. Growth regulators were applied as follows: B nine, 3000 ppm at days 17 and 28 and 1500 ppm day 42.

Classification:

*Botanical.*—*Kalanchoe blossfeldiana,* cultivar 'Patty'.

Parentage:

*Male* (*pollen*) *parent.*—Proprietary *Kalanchoe blossfeldiana* selection #'95316-16'.

*Female* (*seed*) *parent.*—Proprietary *Kalanchoe blossfeldiana* selection #'95013'.

Propagation:

*Type cutting.*—Terminal tip.

*Time to initiate roots.*—Approximately 7–14 days with the shorter times generally being experienced in the summer and the longer times in the winter.

*Time to develop roots.*—Approximately 21 days.

*Root description.*—Fibrous, branching.

Plant description:

*Habit of growth.*—Moderately vigorous with good basal branching. A mature plant, at 16 weeks after the planting of an unrooted cutting, commonly measures approximately 13.6 cm in height and approximately 17.1 cm in width.

*Branching habit.*—Typically forms one main stem 10 cm in length and 4 mm in diameter and 14 lateral branches approximately 7.5 cm in length and 4 mm in diameter. Internode length on main stem: Approximately 1.5 cm.

*Plant form.*—Upright and mounded.

*Foliage.*—Form: Simple. Arrangement: Opposite. Shape: Ovate with obtuse apex, cuneate base and crenate margin. Texture: Glabrous, succulent. Size of mature foliage: Approximately 8.7 cm in length and approximately 5.5 cm in width. Color of mature foliage: Upper surface closest to 137A, lower surface closest to 147B. Petiole length: Approximately 1 cm. Petiole color. 137C. Petiole diameter: Approximately 5 mm.

Flower description:

*Flowering habit.*—Freely flowering.

*Natural flowering season.*—Early January. Flowering time is dependent on temperature, light intensity and other growing conditions.

*Flowering response time.*—Approximately 10 weeks.

*Inflorescence type.*—Dichasial cymes.

*Flowers borne.*—Above foliage.

*Flower longevity.*—Approximately 7 days.

*Fragrance.*—None.

*Quantity of flowers.*—Approximately 37 flowers on main stem and 24 flowers on each lateral branch.

*Flower buds.*—Shape: Elliptical, becoming elongated as it matures. Size just before opening: Length is approximately 1.3 cm, width is approximately 3 mm. Color: 34C.

*Flower.*—Salverform. Corolla: Diameter is approximately 1.6 cm, depth is approximately 4 mm and aspect is slightly cupped. Corolla tube is 9 mm in length, 3 mm in diameter.

*Petals.*—Number: Four. Shape: Obovate with cuspidate apex, rounded base and entire margin. Approximate size: 8 mm in length, 5 mm in width. Aspect: Slightly convex. Texture: Glabrous and velvety.

*Sepals.*—Number: Four. Shape: Lanceolate with acuminate apex and entire margin. Size: 8 mm in length, 1.5 mm in width. Texture: Glabrous. Color. Upper and lower surface: Between 144B and 144C.

*Mature flower color.*—Upper surface of petals is closest to 39A fading to 45C at senescence; lower surface of petals is closest to 31D.

*Peduncle.*—Length: Approximately 1.3 cm in length and 2 mm in diameter.

*Pedicel length.*—Approximately 7 mm.

*Reproductive organs.*—Androecium: 8 stamens arranged in two groups of four — one group being shorter than the other. Anther shape is oblong and flat, length is approximately 0.5 mm. Pollen color is 3B. Gynoecium: Stigma shape is flat, appearance is crystalline, colorless and transparent. Style: Length is approximately 2 mm, color is 154B. Ovary: 4 celled, 7 mm in length, color is 144B.

Seed development: Seed development has not been observed.

Disease resistance: Resistance to known *Kalanchoe* pathogens has not been observed.

TABLE 1

| CHARACTERISTIC | 'PATTY' | 'ARJUNO' |
|---|---|---|
| PLANT HEIGHT | 13.6 cm | 17.6 cm |
| FLOWER DIAMETER | 1.6 cm | 1.5 cm |
| PETAL COLOR-FULLY OPENED- | 39A | Between 44A and 44B |
| APPROXIMATE NUMBER OF FLOWERS PER PLANT | 373 | 548 |

I claim:

1. A new and distinct cultivar of *Kalanchoe* plant named 'Patty' substantially as herein shown and described, which:

(a) exhibits bright orange flowers, (b) forms dark green foliage, (c) exhibits a good basal branching character, and (d) exhibits a compact upright growth habit.

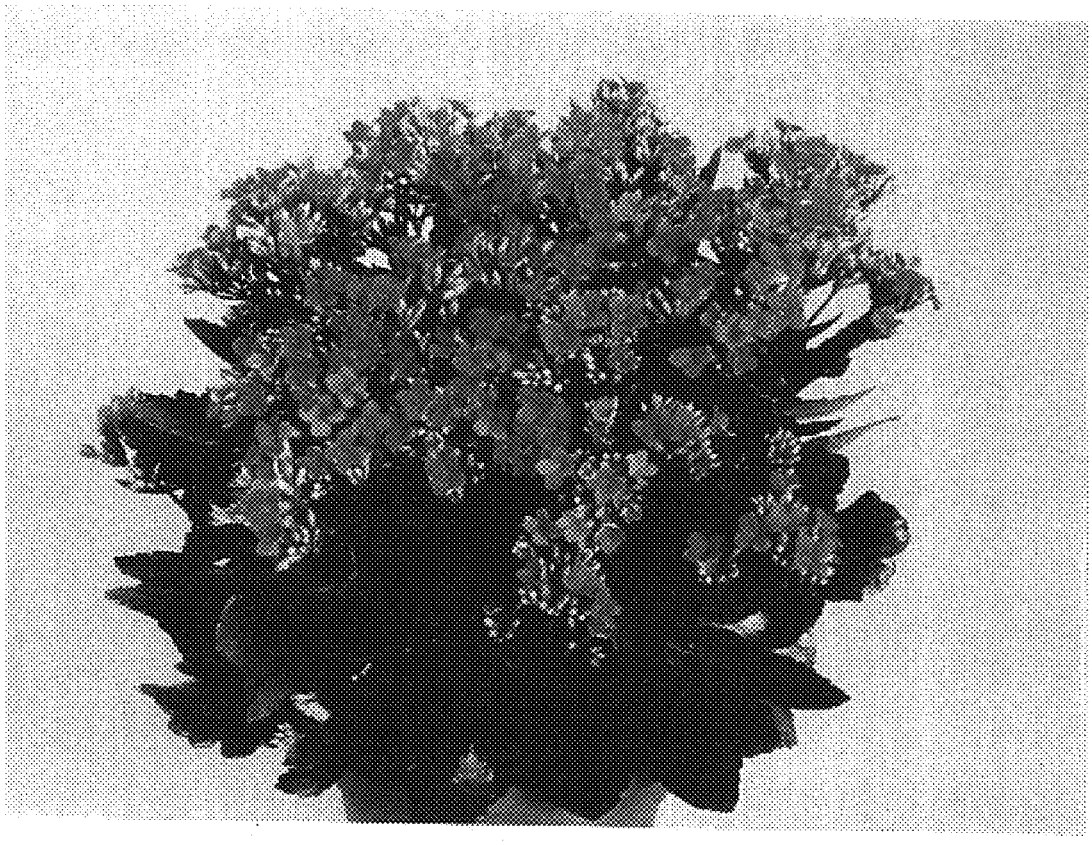

* * * * *